United States Patent
Azzolini

(10) Patent No.: US 7,244,248 B2
(45) Date of Patent: Jul. 17, 2007

(54) FLUID MIXING UNIT, PARTICULARLY FOR MIXING DIAGNOSTIC OR MEDICAL FLUIDS ALONG BIOMEDICAL LINES

(75) Inventor: Graziano Azzolini, Cavezzo (IT)

(73) Assignee: Sidam Di Azzolini Graziano E C. S.A.S., Mirandola (IT)

(*) Notice: Subject to any disclaimer, the term of this patent is extended or adjusted under 35 U.S.C. 154(b) by 240 days.

(21) Appl. No.: 10/698,513

(22) Filed: Nov. 3, 2003

(65) Prior Publication Data

US 2004/0092905 A1 May 13, 2004

(30) Foreign Application Priority Data

Nov. 6, 2002 (IT) .................. MO2002A0321

(51) Int. Cl.
  *A61M 19/00* (2006.01)
  *B67D 3/00* (2006.01)
  *A61M 37/00* (2006.01)
  *A61J 3/00* (2006.01)

(52) U.S. Cl. .................. 604/416; 604/82; 137/896

(58) Field of Classification Search .................. 604/403, 604/416, 6.14, 82, 83, 258, 30; 137/602, 137/896, 886, 127; 222/145.1, 129, 145.5; 366/133, 134, 165.1, 165.2, 339, 341
See application file for complete search history.

(56) References Cited

U.S. PATENT DOCUMENTS

| | | | | |
|---|---|---|---|---|
| 1,519,832 A | | 12/1924 | Griffin | |
| 3,042,038 A | * | 7/1962 | Beacham | 604/127 |
| 3,677,248 A | * | 7/1972 | McPhee | 604/500 |
| 4,053,141 A | * | 10/1977 | Gussefeld | 366/339 |
| 4,522,504 A | * | 6/1985 | Greverath | 366/339 |
| 4,900,480 A | | 2/1990 | Litz et al. | |
| 5,046,856 A | | 9/1991 | McIntire | |
| 5,470,150 A | | 11/1995 | Pardikes | |
| 5,487,606 A | * | 1/1996 | Keller | 366/339 |
| 5,569,181 A | * | 10/1996 | Heilman et al. | 604/30 |
| 5,823,987 A | * | 10/1998 | Elgas et al. | 604/6.13 |

FOREIGN PATENT DOCUMENTS

WO  01 91829  12/2001

* cited by examiner

*Primary Examiner*—Tatyana Zalukaeva
*Assistant Examiner*—Leslie R. Deak
(74) *Attorney, Agent, or Firm*—Browdy amd Neimark, PLLC

(57) ABSTRACT

A fluid mixing unit insertable along conveyance and/or distribution lines, particularly for mixing diagnostic or medical fluids or the like along biomedical lines, comprising a body that is internally hollow and is provided with at least one pair of intake ports for introducing two fluids to be mixed, which are associable with respective feeder devices, and a discharge port for discharging the mixture of the two fluids, which is associable with an outflow device, and a duct for the flow and mixing of the two fluids that is formed in the body and is connected to the intake ports and to the discharge port.

26 Claims, 2 Drawing Sheets

FLUID MIXING UNIT, PARTICULARLY FOR MIXING DIAGNOSTIC OR MEDICAL FLUIDS ALONG BIOMEDICAL LINES

BACKGROUND OF THE INVENTION

The present invention relates to a fluid mixing unit that can be inserted along conveyance and/or distribution lines, particularly for mixing diagnostic or medical fluids or the like along biomedical lines.

With particular but not exclusive reference to the biomedical sector related to imaging diagnostics, it is known that some investigation methods, such as for example computerized axial tomography, angiography, coronarography and others, entail administering contrast media, based for example on iodine, to the patients.

The nature and/or concentration of the contrast media varies according to the type of investigation to be performed.

For this very reason, a range of various packages is currently commercially available for each type of contrast medium, and said packages differ from each other in the concentration of iodine diluted in suitable vehicles.

This causes drawbacks, including the fact that the production of packages at different concentrations of the contrast media is very complex, slow and expensive, and the fact that radiology wards must acquire diversified stockpiles of the various packages, sustaining substantial procurement, management and stocking costs.

The execution of certain investigation techniques, moreover, requires the administration, for example intravenously, of boluses of physiological solutions, water or other equivalent liquids, alternated with boluses of contrast media: the two fluids mix with each other only after they have been injected into the patients.

SUMMARY OF THE INVENTION

The aim of the present invention is to eliminate the above-noted drawbacks, by providing a fluid mixing unit that can be inserted along conveyance and/or distribution lines, particularly for mixing diagnostic or medical fluids or the like, along biomedical lines, which allows to mix at the time of use two or more fluids, particularly contrast media and a respective dilution vehicle (physiological solution, water or other), in the intended proportions, which can vary as a function of the use of the resulting mixture, i.e., in particular, according to the imaging diagnostics technique to be performed.

Within this aim, an object of the present invention is to simplify the production of packages of contrast media and to contain their times and costs.

Another object of the present invention is to reduce the stockpiles of packages of contrast media of radiology wards, simplify their management and limit their maintenance and stocking costs.

Another object of the present invention is to provide a fluid mixing unit that is simple, relatively easy to provide in practice, safe in use, effective in operation, and has a relatively low cost.

This aim and these and other objects that will become better apparent hereinafter are achieved by the present fluid mixing unit insertable along conveyance and/or distribution lines, particularly for mixing diagnostic or medical fluids or the like along biomedical lines, characterized in that it comprises a body that is internally hollow and is provided with at least one pair of intake ports for introducing two fluids to be mixed, which are associable with respective feeder devices, and a discharge port for discharging the mixture of the two fluids, which is associable with an outflow device, and a duct for the flow and mixing of the two fluids that is formed in said body and is connected to said intake ports and to said discharge port.

BRIEF DESCRIPTION OF THE DRAWINGS

Further characteristics and advantages of the present invention will become better apparent from the following detailed description of some preferred but not exclusive embodiments of a fluid mixing unit insertable along conveyance and/or distribution lines, particularly for mixing diagnostic or medical fluids or the like, along biomedical lines, illustrated by way of nonlimiting example in the accompanying drawings, wherein.

DESCRIPTION OF THE PREFERRED EMBODIMENTS

Figure 1:
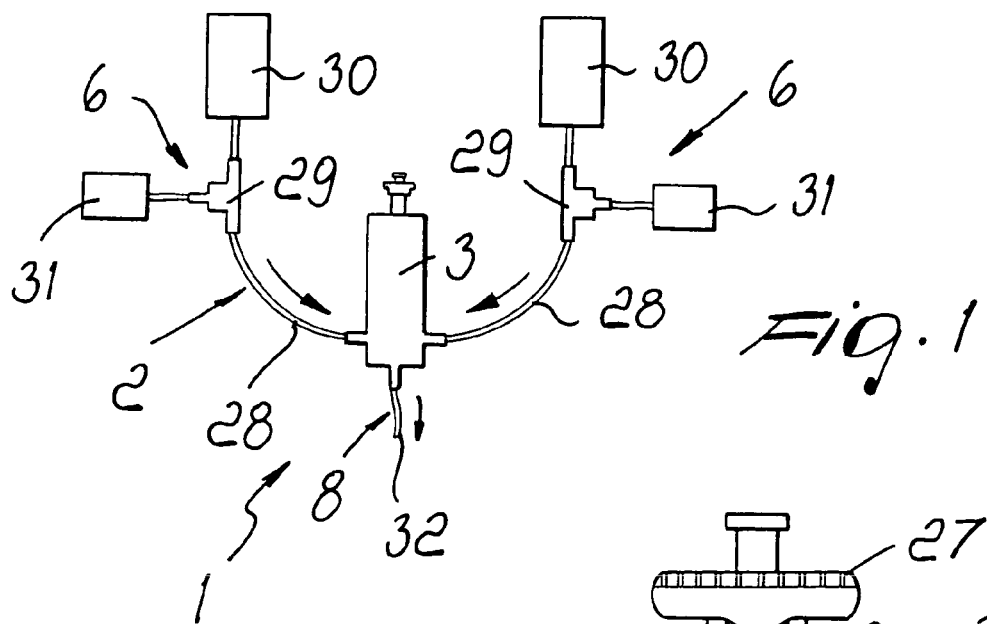
FIG. 1 is a schematic view of a unit according to the invention, inserted along a biomedical line.

With reference to the figures, the reference numeral 1 generally designates a fluid mixing unit that can be inserted along conveyance and/or distribution lines, particularly for mixing diagnostic or medical fluids or the like, along biomedical lines.

The unit 1 can be inserted, for example, along a biomedical line 2 for administering to patients diluted contrast media, in the chosen proportions, in physiological solution, water or other equivalent liquid, in order to perform imaging diagnostics techniques, such as for example angiography, coronarography, computerized axial tomography or others.

The unit 1 comprises a body 3, which is substantially cylindrical and internally hollow and is provided at one end with two intake ports 4 and 5 for two fluids to be mixed, each port being associable with a respective fluid feeder device 6, and with a discharge port 7 for discharging the mixture of the two fluids that is associable with an outflow device 8 and, at the opposite end, with an exit opening 9 for the gases contained or generated inside it.

A duct 10 for the flow and mixing of the two fluids is formed inside the body 3 and is connected to the two intake ports 4 and 5, to the discharge port 7, and to the exit opening 9.

At least one portion of the duct 10 is substantially shaped like a spiral, helix or the like, and is constituted by two consecutive portions 10a and 10b, which are connected to each other and have opposite flows: the portion 10b is internal and the portion 10a is external, i.e., the portion 10b is formed inside the volume delimited by the portion 10a.

The outer portion 10a has an end 11 that is adjacent and connected to the end 12 of the inner portion 10b; a connector, such as a spoked partition 13, connects the two ends 11 and 12 of the two portions 10a and 10b to each other and to the exit opening 9.

The outer portion 10a is associated with the two intake ports 4 and 5 and is crossed, in an ascending direction, by the two mixing fluids, while the inner portion 10b is associated with the discharge port 7 of the mixture and is crossed in a descending direction by the two mixing fluids.

The outer portion 10a is delimited by the inner lateral surface 14 of the body 3 and by the outer lateral surface 15 of a first element 16, which is substantially cylindrical and is inserted substantially coaxially and snugly in the body 3.

The outer lateral surface 15 of the first element 16 is substantially shaped like a helix, spiral or the like; in particular, it can be constituted by the intersection of two threads shaped like a helix, spiral or the like that have mutually opposite winding directions.

The inner portion 10b is delimited by the outer lateral surface 17 of a second element 18, which is substantially cylindrical and is inserted, substantially coaxially and snugly, in a respective seat 19 formed inside the first element 16, and by the internal wall 20 of the seat 19.

The outer lateral surface 17 of the second element 18 is shaped substantially like a helix, spiral or the like; in particular, it can be constituted by a single thread shaped like a helix, spiral or the like.

The spoked partition 13 forms a plurality of passages 21 for connecting the ends 11 and 12 of the two portions 10a and 10b and the exit opening 9.

The exit opening 9 is associated with venting means which, for example, can be constituted by a floater valve 22 of the normally-open type. The valve 22 is constituted by a guiding body 23, which accommodates the floater constituted for example by a ball 24.

As long as the ball 24 rests on the partition 13, the gases inside the body 3 exit from the exit opening 9; once the gases have been expelled, the hydrostatic thrust applied by two fluids introduced in the duct 10 causes the ball 24 to rise and abut against a respective abutment seat, constituted for example by a gasket 25, in order to close the exit opening 9.

The gasket 25 is recessed in a respective annular seat formed in a closure cap 26 in which the exit opening 9 is formed.

The exit opening 9, moreover, is associated with filtering means 27, preferably, but not exclusively, of the hydrophobic type which are arranged downstream of the valve 22.

Each feeder device 6 can be constituted, for example, by a duct 28 in which one end is associated with the respective intake port 4 or 5 and the opposite end associated with a three-way valve 29, not shown in detail, which is connected to a reservoir or bottle 30 of fluid and to a control injector 31.

The two ways of the valve 29 that are associated with the reservoir 30 and with the duct 28 are controlled by a respective unidirectional flow control element; the other way, the one associated with the injector 31, is instead pervious.

The two unidirectional flow control elements are mutually opposite; the way associated with the reservoir 30 is used for the inflow of the fluid into the valve 29, while the way associated with the intake port 4 or 5 is used for the outflow of the fluid from the valve 29.

A chamber connected to the injector 31 and to the two mutually opposite unidirectional flow control elements are formed inside the valve 29.

The injector 31 can be constituted for example by a syringe: by actuating the plunger of the syringe, the two unidirectional flow control elements are activated alternately in order to transfer the fluid from the reservoir 30 into the chamber of the valve 29 and into the injector 31 and then propel it into the duct 28.

By means of the injectors 31 it is possible to adjust the doses of the two fluids introduced in the unit 1.

The outflow device 8 can be constituted for example by a tube 32 in which one end is connected to the discharge port 7 and the opposite end is provided with injection means, such as conventional needles, for intravenous or arterial administration of the mixture to patients.

Figure 3:
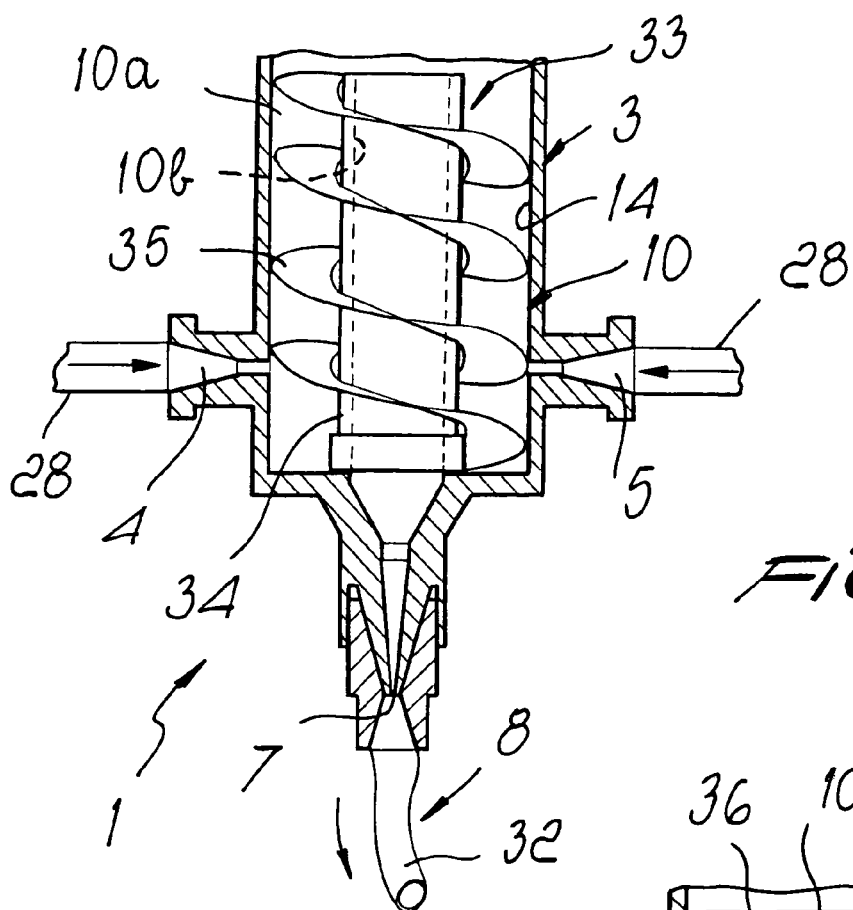
FIG. 3 is a schematic sectional view, taken along a longitudinal plane, of a detail of a first alternative embodiment of the unit according to the invention.
Figure 4:
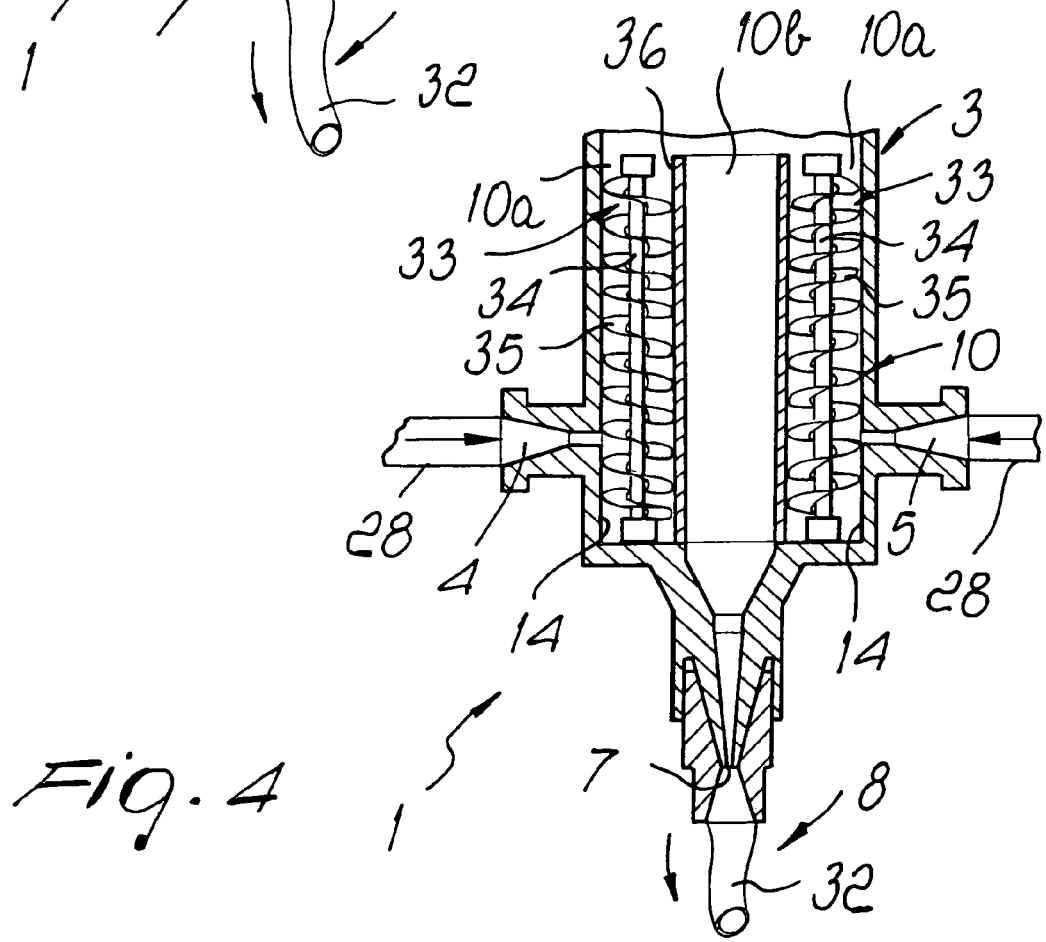
FIG. 4 is a schematic sectional view, taken along a longitudinal plane, of a detail of a second alternative embodiment of the unit according to the invention.

FIGS. 3 and 4 illustrate two alternative embodiments of the unit 1, in which an impeller 33 is inserted along the duct 10 for the flow and mixing of the two fluids; said impeller is constituted by a shaft 34 around which a set of vanes 35, substantially shaped like a helix or the like, is wrapped.

In FIG. 3, the impeller 33 is inserted substantially coaxially in the body 3; the outer portion 10a of the duct 10 is formed by the outer lateral surface of the set of vanes 35 and by the inner lateral surface 14 of the body 3, while the inner portion 10b is formed by a channel formed inside the shaft 34.

In FIG. 4, the inner portion 10b is formed by a tube 36 that is inserted coaxially in the body 3; along the outer annular ring that surrounds the tube 36 there are at least two impellers 33 that are distributed radially, each impeller forming a respective outer portion 10a that is associated with a respective intake port 4 or 5.

Figure 2:
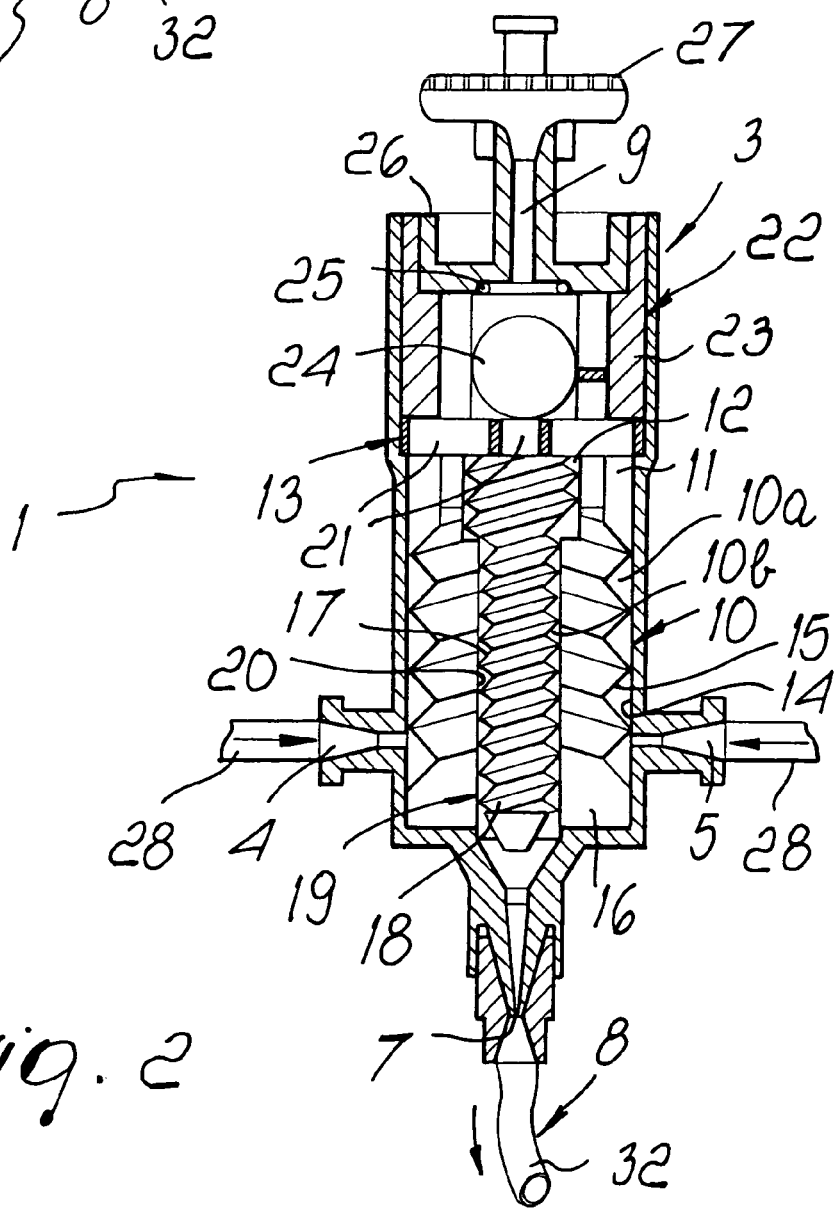
FIG. 2 is a schematic sectional view, taken along a longitudinal plane, of the unit according to the invention.

With particular reference to FIGS. 1 and 2, the operation of the invention is as follows:

The feeder devices 6 introduce under pressure in the body 3 chosen and predefinable quantities of the two fluids to be mixed, which are contained in the reservoirs 30.

The two fluids flow in an ascending direction along the outer portion 10a, along which they begin to mix together by way of the intersection between the mutually opposite helical threads; once the end 11 has been reached, the two fluids flow through the ports 21 of the spoked partition 13 and fall into the inner portion 10b, which they cross in a descending direction, further mixing uniformly with each other, until they reach the vicinity of the discharge port 7, from which they flow out toward the outflow device 8.

The gases and air that are contained and formed in the body 3 are evacuated through the valve 22 and the exit port 9.

The filtering means 27 of the hydrophobic and sterilizing type ensure the exit of only gases and air, ensuring the administration of fluid alone to the patients.

The mixed fluids can be constituted for example by a contrast medium for imaging diagnostics, such as iodine or the like, and by a diluting vehicle, such as for example physiological solution, water or the like.

The dosage of the two fluids and their mixing occur along the line just before they are administered to the patients.

The feeder devices 6 allow to regulate and vary continuously the doses of the two fluids to be mixed.

Advantageously, the line 2, the unit 1 and the feeder devices 6 are kept at a same average temperature so as to uniform the mixing process of the two fluids and avoid the formation of currents and turbulent motions as a consequence of temperature gradients.

In practice it has been found that the described invention achieves the intended aim and objects.

The unit according to the invention allows in fact to mix two or more fluids in the chosen quantities and proportions along the line over conveyance and distribution networks.

In particular, it allows to eliminate the production of a diversified range of packages of contrast media at different concentrations and the stockpiling of various packages by radiological wards, surgeries and imaging diagnostics laboratories; it is in fact sufficient to have available packages of contrast media at the maximum possible concentration and then dilute them at the time of use in the proportions and quantities chosen directly along the lines for administration to patients.

The invention thus conceived is susceptible of numerous modifications and variations, all of which are within the scope of the appended claims.

All the details may further be replaced with other technically equivalent ones.

In practice, the materials used, as well as the shapes and dimensions, may be any according to requirements without thereby abandoning the scope of the protection of the appended claims.

The disclosures in Italian Patent Application No. MO2002A000321 from which this application claims priority are incorporated herein by reference.

What is claimed is:

1. A fluid mixing unit for mixing diagnostic or medical fluids along biomedical lines, comprising: a body that is internally hollow and is provided with at least one pair of intake ports for introducing two fluids to be mixed, said intake ports being connectable to respective feeder devices, and with a discharge port for discharging a mixture of the two fluids, said discharge port being connectable to an outflow device; and a duct shaped so as to enable flow and mixing of the two fluids, said duct being formed in said body and being connected to said intake ports and to said discharge port;
   wherein at least one portion of said duct is substantially shaped as a spiral or helix;
   wherein said body comprises an opening for exit of gases contained or generated inside the unit, said opening being associated with said duct; and
   further comprising gas venting means associated with the opening for exit of gases.

2. The unit of claim 1, wherein said duct comprises at least two consecutive portions that are connected to each other and are arranged so as to be crossed by mutually opposite flows, a first one of said portions being associated with said intake ports, and a second one being associated with said discharge port.

3. The unit of claim 2, comprising a connector for said two portions and said gas exit opening.

4. The unit of claim 3, wherein said connector comprises a partition having passages for connecting adjacent ends of said two portions and said gas exit opening.

5. The unit of claim 2, wherein an inner one of said portions is formed inside a volume delimited by the other, outer portion.

6. The unit of claim 5, wherein one of said two portions is provided for ascending flow and the other one for descending flow.

7. The unit of claim 6, wherein said outer portion is associated with said intake ports and is provided for ascending flow, the inner portion being associated with said discharge port and being provided for descending flow.

8. The unit of claim 5, comprising at least one impeller inserted along said duct for the flow and mixing of the two fluids.

9. The unit of claim 8, wherein said impeller is constituted by a shaft with a set of vanes wrapped therearound, said set of vanes being shaped substantially like a helix.

10. The unit of claim 8, wherein said impeller is inserted in said duct substantially coaxially to said body, said outer portion being formed by an outer lateral surface of the impeller and by an inner lateral surface of said body.

11. The unit of claim 10, wherein said inner portion is formed by a channel arranged inside said shaft.

12. The unit of claim 10, wherein said inner portion is formed by a tube around which at least two said outer portions are distributed radially, each one of said outer portions being associated with a respective said intake port.

13. The unit of claim 2, wherein each one of said two portions has an end thereof that is adjacent and connected to an end of the other portion.

14. The unit of claim 2, wherein said body is substantially cylindrical, said mixture discharge port and said gas exit opening being formed, respectively, proximate to opposite ends of the body and said intake ports being formed proximate to said mixture discharge port.

15. The unit of claim 2, comprising a first substantially cylindrical element, which is inserted substantially coaxially inside said body and is provided with a contoured outer lateral surface, said outer portion being formed by an inner lateral surface of said body and by an outer lateral surface of said first substantially cylindrical element.

16. The unit of claim 15, wherein said outer lateral surface of the first substantially cylindrical element is shaped as a spiral or a helix.

17. The unit of claim 16, wherein said outer lateral surface of the first substantially cylindrical element is formed by intersection of two threads, shaped as a helix or as a spiral, that have mutually opposite winding directions.

18. The unit of claim 15, comprising a second substantially cylindrical element, which is inserted substantially coaxially in a respective seat formed in said first substantially cylindrical element and is provided with a contoured outer lateral surface, said inner portion being formed by a wall of said seat and by an outer lateral surface of said second substantially cylindrical element.

19. The unit of claim 18, wherein said outer lateral surface of the second substantially cylindrical element is shaped as a spiral or as a helix.

20. The unit of claim 1, wherein said venting means comprises a floater valve.

21. The unit of claim 20, wherein said valve is normally open.

22. The unit of claim 1, comprising filtering means that are associated for fluid filtering with said gas exit opening.

23. The unit of claim 22, wherein said filtering means are of a hydrophobic type.

24. A fluid mixing unit for mixing diagnostic or medical fluids along biomedical lines, comprising: a body that is internally hollow and is provided with at least one pair of intake ports for introducing two fluids to be mixed, said intake ports being connectable to respective feeder devices, and with a discharge port for discharging a mixture of the two fluids, said discharge port being connectable to an outflow device; and a duct shaped so as to enable flow and mixing of the two fluids, said duct being formed in said body and being connected to said intake ports and to said discharge port;

wherein at least one portion of said duct is substantially shaped as a spiral or helix;

wherein feeder devices are provided that comprise each a three-way valve, in which two ways are provided for flow control with a respective unidirectional flow control element, and are each respectively associated with a fluid reservoir and with one of said intake ports, a third way being provided pervious and associable with a control injector.

25. The unit of claim 24, wherein said three-way valve comprises an internal chamber that is connected to the ways thereof.

26. The unit of claim 24, wherein said unidirectional flow control elements are opposite to each other, the way associable with the reservoir being provided for inflow of fluid into the three-way valve and the way associable with the intake port being provided for outflow of fluid from the three-way valve.

* * * * *